(12) United States Patent
Lindenberg et al.

(10) Patent No.: US 9,936,166 B2
(45) Date of Patent: Apr. 3, 2018

(54) METHOD FOR PLANNING A DENTAL TREATMENT

(71) Applicant: Sirona Dental Systems GmbH, Bensheim (DE)

(72) Inventors: Kai Lindenberg, Wersau (DE); Ciamak Abkai, Heddesheim (DE)

(73) Assignee: Sirona Dental Systems GmbH, Bersheim (DE)

( * ) Notice: Subject to any disclaimer, the term of this patent is extended or adjusted under 35 U.S.C. 154(b) by 274 days.

(21) Appl. No.: 14/646,095

(22) PCT Filed: Nov. 19, 2013

(86) PCT No.: PCT/EP2013/074139
§ 371 (c)(1),
(2) Date: May 20, 2015

(87) PCT Pub. No.: WO2014/079830
PCT Pub. Date: May 30, 2014

(65) Prior Publication Data
US 2015/0296184 A1   Oct. 15, 2015

(30) Foreign Application Priority Data

Nov. 22, 2012 (DE) .................. 10 2012 221 374

(51) Int. Cl.
*H04N 7/18* (2006.01)
*A61C 9/00* (2006.01)
(Continued)

(52) U.S. Cl.
CPC ............. *H04N 7/18* (2013.01); *A61C 9/0046* (2013.01); *G01B 11/254* (2013.01);
(Continued)

(58) Field of Classification Search
CPC ... A61C 9/0046; G01B 11/254; G06T 7/0012; H04N 13/02; H04N 5/265; H04N 7/18
See application file for complete search history.

(56) References Cited

U.S. PATENT DOCUMENTS 6,068,482 A    5/2000  Snow
6,072,903 A *  6/2000  Maki ....................... G06T 7/251
                                                       348/169

(Continued)

FOREIGN PATENT DOCUMENTS

WO      2009/145391 A1    12/2009

OTHER PUBLICATIONS

International Search Report dated Mar. 27, 2014, International Application No. PCT/EP2013/074139.

(Continued)

*Primary Examiner* — Peter D Le
(74) *Attorney, Agent, or Firm* — Fitzpatrick, Cella, Harper & Scinto

(57) ABSTRACT

The invention relates to a method for planning or for checking the planning of a dental and/or a maxillofacial treatment, wherein at least one video recording of an object (3) is recorded by means of at least one video camera (1). A patient model (4) is available which comprises image data of the object (3), wherein the video recording is virtually coupled to the patient model (4) in such a way that a viewing direction (13) of the view of the patient model (4) is changed in dependence on a changing recording direction (9, 46, 47, 48, 49, 50) of the video recording when the video camera (1) is moved in relation to the object (3).

29 Claims, 2 Drawing Sheets

(51) Int. Cl.
*G01B 11/25* (2006.01)
*G06T 7/00* (2017.01)
*H04N 5/265* (2006.01)
*H04N 13/02* (2006.01)

(52) U.S. Cl.
CPC .......... *G06T 7/0012* (2013.01); *H04N 5/265* (2013.01); *H04N 13/02* (2013.01)

(56) References Cited

U.S. PATENT DOCUMENTS

| | | | |
|---|---|---|---|
| 2003/0169913 A1 | 9/2003 | Kopelman et al. | |
| 2004/0029068 A1* | 2/2004 | Sachdeva | A61C 7/00 433/24 |
| 2004/0197727 A1 | 10/2004 | Sachdeva et al. | |
| 2005/0142517 A1* | 6/2005 | Frysh | A61C 13/0004 433/173 |
| 2006/0120582 A1* | 6/2006 | Squilla | A61C 13/0004 382/128 |
| 2007/0064242 A1* | 3/2007 | Childers | G01B 11/24 356/601 |
| 2008/0318179 A1* | 12/2008 | Liu | A61C 7/00 433/24 |
| 2013/0172731 A1* | 7/2013 | Gole | A61B 5/0035 600/424 |

OTHER PUBLICATIONS

Office Action dated Jul. 30, 2013, in German Patent Appln. No. 10 2012 221 374.0.
International Preliminary Report on Patentability dated Dec. 11, 2014, International Application No. PCT/EP2013/074139.
Written Opinion of the International Search Authority dated Nov. 22, 2014, International Application No. PCT/EP2013/074139.

\* cited by examiner

METHOD FOR PLANNING A DENTAL TREATMENT

TECHNICAL FIELD

The invention relates to a method for planning a dental treatment, wherein at least one video recording of an object to be treated is recorded by means of at least one video camera.

PRIOR ART

Several methods for planning dental treatments are known from the prior art.

In a first known method, the planning is performed directly with patients, wherein the treating dentist examines the patient's dental situation for diseased areas and then notes possible treatments and makes comments on the individual dental areas. Precise planning of the dimensions, orientations and positions of the denture parts or implants to be inserted are then usually planned in detail with a model of the dental situation.

Alternatively, the denture parts or implants to be inserted can also be planned on the basis of three-dimensional X-ray data,
on which optical three-dimensional surface data of the dental situation may be superimposed. The planning may therefore be purely virtual, without having to prepare an actual impression model of the dental situation.

US 2004/0197727 A1 discloses a method and a workstation for planning an orthodontic treatment for a patient. The workstation has a computer and a graphical user interface, wherein 3D image data of the patient is displayed by means of the graphical user interface. The insertion of denture parts as well as other dental treatments can also be simulated. Several types of 3D image data such as optical intraoral images, X-ray data, CT scans, intraoral colored photographs of the teeth and virtual 3D dental models
can also be superimposed to create a virtual patient model. The virtual patient model can therefore represent not only the patient's facial surfaces but also internal structures such as dental roots and jawbones. Traditional CAD software tools can be used to observe this virtual patient model. The virtual patient model can be observed from each direction, or only sectional views in defined planes may be displayed.

Characteristic matching points may be used for orientation of the individual 3D data sets, for example, on the 3D X-ray image of the jaw and in the three-dimensional optical image of the facial surfaces to calculate a transformation matrix.

One disadvantage of the aforementioned methods is that the planning is complex, taking place in several steps, wherein volume data sets of the dental situation, such as three-dimensional X-ray data and/or optical surface data are generated at first, and only then is planning performed using planning software on the basis of these volume data sets.

The object of the present invention is therefore to provide a method for planning a dental treatment that will permit simple, rapid and better planning.

DESCRIPTION OF THE INVENTION

The invention relates to a method for planning or checking the planning of a dental and/or maxillofacial treatment, wherein a video recording is made of an object, such as the head of a patient to be treated, by using at least one video camera.

A patient model is available comprising the image data of the object. The video recording is coupled virtually to the patient model, so that the direction of viewing the patient model changes when the video camera is moved in relation to the object, depending on the changing recording direction of the video recording. A section of the patient model to be displayed is defined by a distance of the video camera in relation to the object and by a recording direction of the video camera in relation to the object.

The dental treatment to be planned may comprise, for example, analysis of the dental situation in diseased regions and the determination of possible therapies. The therapeutic options may be preparations to be made, denture parts to be placed on preparations or implants to be inserted, for example. The video recording may be made, for example, using a clear motion rate
of 50 Hz. The object to be recorded may be, for example, a mandible, a maxilla, a group of teeth and/or the patient's entire head. Alternatively, however, the object to be recorded may also be an impression model of the dental situation with which the planning is to be performed. The patient model which is already available comprises recorded image data such as three-dimensional optical image data, three-dimensional X-ray data and/or MRI scan data. The video recording of the object is coupled to the available patient model so that the virtual direction of viewing the patient model follows the recording direction of the video camera. The direction of viewing the representation of the patient model may correspond to the recording direction of the video camera, for example.

In addition to the image data, the patient model may also comprise additional information about the dental situation, such as the bone density of the jawbone, in order to perform a mechanical load simulation in planning an implantation, for example.

The treating dentist may therefore also aim the video camera at a certain region of the patient's head, wherein the patient model is represented by means of a monitor from the corresponding direction of view, for example. This greatly makes it easier for the dentist to orient and plan the dental treatment. The dentist can also approach a certain region more closely with the video camera, wherein only the corresponding section from the three-dimensional X-ray image data of the patient model is represented.

The patient model may advantageously comprise three-dimensional optical surface data, three-dimensional X-ray data, virtual planning data and/or MRI scan data of at least one part of
the object.

The three-dimensional optical surface data can be generated by a fringe projection method, for example. The three-dimensional X-ray data can be generated, for example, by a DVT measurement method or a computer tomography method (CT). The image data of the patient model may also comprise only a part of the object. If the object is the patient's entire head, then the X-ray data may comprise, for example, only the maxilla or only the mandible. The patient model may also comprise X-ray data of a two-dimensional cephalometric X-ray or a panorama image. The virtual planning data may comprise, for example, planning elements such as virtual marks, comments, simple drawings or models of denture parts to be inserted and/or implants, which have a fixed positional relationship to the surrounding dental situation consisting of teeth and gingiva.

The video recording may advantageously be displayed as superimposed on the patient model using at least one display device such as a monitor.

The video recording may be represented, for example, as semitransparent with the patient model being faded in. This makes it easy for the treating dentist to be orientated in relation to the patient. Alternatively, the patient model may be displayed on the monitor alone, with the video recording being used only for determination of the recording direction.

Alternatively, the display device may be virtual monitor spectacles, wherein the navigation in virtual reality in relation to the patient model is achieved by moving the monitor spectacles in relation to the patient.

Other displaying or fading-in virtual reality display devices (English: augmented reality) may also be used as the display device.

In another alternative, the display device may be a so-called tablet computer or a portable PDA (personal digital assistant) computer, wherein the video recording is generated by means of the video camera integrated into the tablet computer or into the portable PDA computer. The patent model is then displayed depending on the movement of the tablet computer or the portable PDA computer from the corresponding viewing direction by means of the monitor of the tablet computer or the portable PDA computer.

The virtual coupling of the video recording to the patient model can advantageously take place using pattern recognition algorithms. Marks made on the object or characteristic structures of the object such as the patient's eyes, nose, mouth or teeth may be recognized in the video recording as well as in the patient model in order to establish a correspondence between the video recording and the patient model.

When using pattern recognition algorithms, corresponding regions in the video recording and in the patient model are determined and used for determining the orientation of the video recording and the patient model to one another. The corresponding regions may be, for example, characteristic shapes such as the patient's chin or the two angles of the jawbone.

Alternatively, marks may also be applied directly to the object; for example, optical marks may be applied directly to the skin in the area of the patient's cheeks. These marks are then detected in the video recording as well as in the patient model and are used to ascertain the orientation of the video recording in relation to the patient model and to ascertain the recording direction of the video camera in relation to the object. The marks may be detected in a fully automatic process by using a computer algorithm that searches the video recording for a certain pattern of marks. The video recording may also be coupled to the patient model before performing the planning in an initial registration, wherein the recordings of the marks in the video recording can be assigned manually to the recordings of the marks in the patient model.

The coupling between the video recording and the patient model may also be accomplished manually by a user, wherein corresponding points in the video recording and in the patient model are defined.

Advantageously, the changing recording direction of the video camera in relation to the object may be automatically determined with the support of a computer by tracking the marks made on the object, or tracking characteristic structures of the object such as the patient's eyes, nose, mouth or teeth.

The changing recording direction of the video camera is thus determined by a tracking method in which the position of the marks or of the characteristic structures is tracked in the video recording. Depending on the changing recording direction, the corresponding direction of viewing the patient model is calculated, and the corresponding section of the patient model from the calculated viewing direction is displayed on a monitor.

The planning may advantageously take place directly during the video recording, wherein planning elements are displayed as superimposed on the patient model by using a display device, and their positions in relation to the patient model are set by the user.

The treating dentist can therefore add the planning elements such as marks, comments, drawings or models of denture parts and/or implants to the patient model, and their positions in the dental situation can be defined. This takes place directly on the patient simultaneously with the video recording so that the treatment time is shortened and possible mistakes are prevented even during planning.

The planning elements may advantageously be marks, comments, simple drawings or models of denture parts and/or implants to be inserted, the position of which is fixed in relation to the patient model.

The treating dentist may add marks in certain regions of the dental situation to be treated and can provide them with comments which include a diagnosis. The marks may be simple free-hand strokes or prefabricated symbols supplied by software. The comments may be free text entered on a keyboard in a position defined by using a mouse. The positions of the planning elements in relation to the patient model are therefore defined so that the planning elements can be rotated together with the patient model when the direction of viewing the patient model changes.

The planning elements may advantageously be projected directly onto the object to be treated by means of a projector.

The projector may be a traditional optical projector which projects the planning elements directly onto the skin surface or the patient's teeth. In this way, the planning can take place directly on the patient so that no display device is needed for displaying the planning elements.

The planning may advantageously be performed by means of a marker, wherein an optical pointer is projected onto the patient who then is detected by the video camera during the video recording.

The optical pointer serves as a virtual tool for selecting and shifting the planning elements within the patient model projected onto the patient. In this way, the individual planning elements, such as comments or marks, can be added and shifted by using the optical marker. The position of the planning elements is then defined in relation to the patient model.

The optical marker may advantageously be a laser pointer which projects a laser point onto the object.

By using the laser pointer as an optical marker, the treating dentist can also perform the planning from a greater distance. The laser point is of such a color that it can be detected unambiguously in the video recording.

The planning may advantageously take place by using an optically detectable marker which is detected by the video camera during the video recording.

Therefore, the treating dentist can navigate by using the marker like a pen and can select certain regions of the patient model.

The visually detectable marker may advantageously be a finger, a dental instrument or a pen having a colored tip.

The planning elements projected onto the object can advantageously be selected and shifted by using the marker to define their positions in relation to the patient model.

With the marker, the treating dentist can therefore select the individual planning elements such as marks, comments, drawings or models of denture parts and/or implants to be inserted, and shift them in relation to the patient model to define their positions.

One of the planning elements may advantageously be selected by the user operating a switch on the marker so that a certain structure is projected onto the surface of the object to be treated, and this structure is discernible in the video recording.

The switch on the marker may have any design and may be embodied as a button, for example. In operation of this switch, the structure is projected onto the object, which may be embodied as a certain pattern to be faded in, a color change of the optical mark, a change in shape of the optical mark or as a blind code, for example. An action such as the selection of a certain planning element is triggered by depressing the button. The respective planning element can be shifted as long as the button remains depressed. When the button is released, the planning element is released from the optical mark, and the position of this planning element in relation to the patient model is thereby defined.

To facilitate the planning, the image data and/or the virtual planning data of the patient model can advantageously be projected by a projector onto the object to be treated.

As an alternative to representing the patient model on a monitor, the patient model can be projected onto the patient's skin surface by the projector. Therefore, X-ray images of a jawbone structure can be projected onto the respective region of the skin surface, for example, to facilitate the orientation for the treating dentist.

BRIEF DESCRIPTION OF THE DRAWINGS

The invention will be explained on the basis of the drawings, in which.

EXEMPLARY EMBODIMENT

Figure 1:
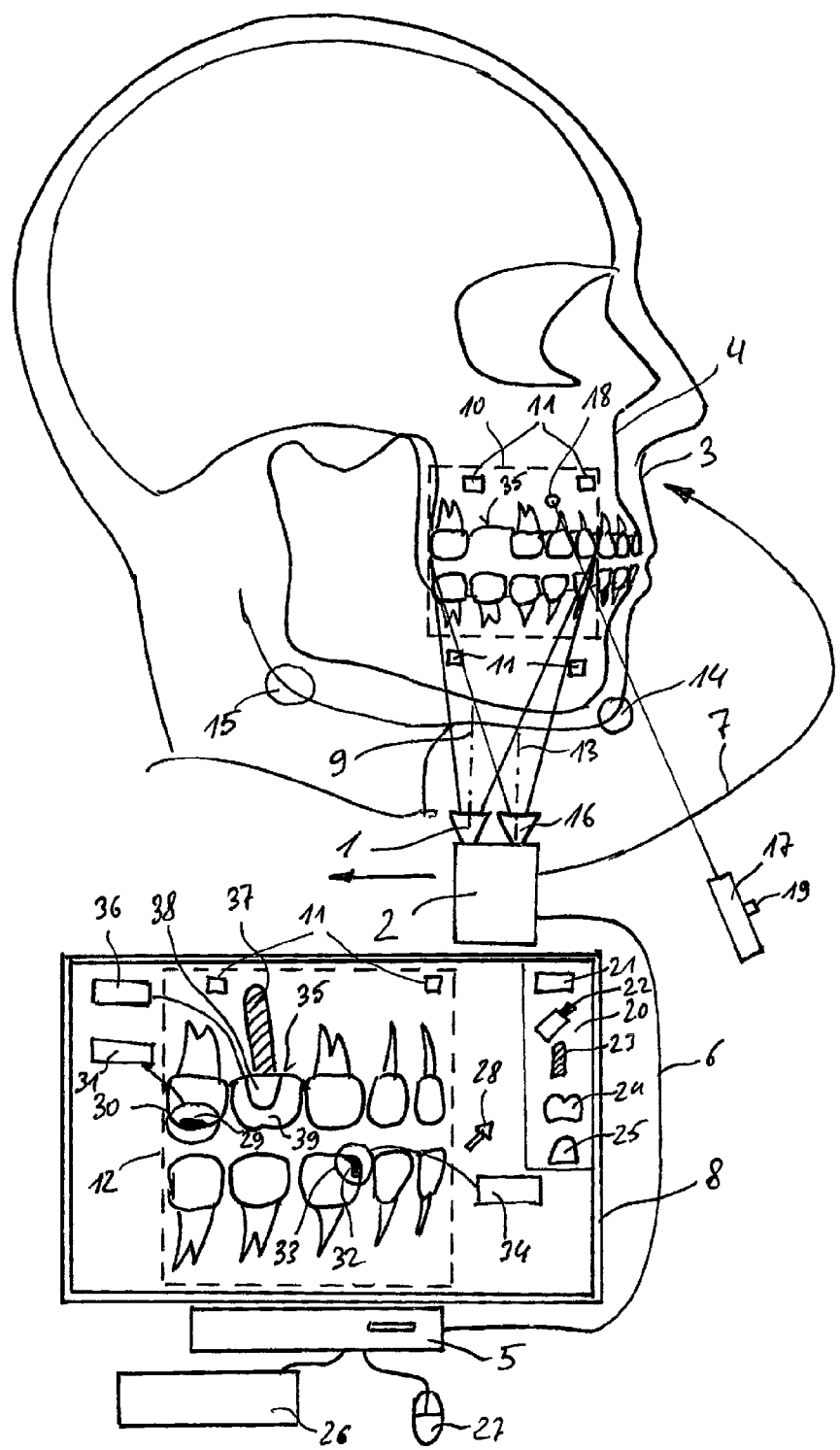
FIG. 1 shows a diagram to illustrate the method for planning a dental treatment.

FIG. 1 shows a diagram to illustrate the method for planning a dental treatment. A video recording of an object 3 to be treated is recorded by using a video camera 1 arranged on a handpiece 2. The object 3 in this case is a patient's head. The video recording thus records the skin surface in the cheek area of the head 3. A patient model 4 that is already available comprises image data already recorded of the object 3, such as three-dimensional X-ray data of the object 3 in the present case. The patient model 4 may also have additional image data such as three-dimensional optical image data and/or MRI scan data of the object 3. The image data of the patient model is stored in an image memory in a computer 5. The image data of the video recording is transmitted from the video camera 1 to the computer 5 via a cable connection 6. The image data of the video camera 1 may also be transmitted wirelessly to a computer 5. The video recording of the object 3 is linked virtually to the patient model 4 so that when the video camera 1 is moved around the object 3 along a path of movement 7, the representation of the patient model 4 is adapted by using a monitor 8 to a changing recording direction 9 of the video camera 1. The video camera 1 records a first section 10 of the skin surface of the object 3. In the analysis of the image data of the video recording by the computer 5, marks 11 placed on the object 3 can be detected. Then the exact position of the object 3 in relation to the video camera 1 is calculated on the basis of the positions of the marks 11. Next, a second section 12 of the patient model 4 is represented on the monitor 8, the section corresponding in its dimensions to the first section 10 from the video recording. The treating dentist can therefore move the video camera 1 around the patient 3 at will and direct it at the relevant regions. The monitor 8 then automatically displays the corresponding section 12 of the corresponding patient data, such as the X-ray data from a viewing direction which corresponds to the recording direction of the video camera, for example. Before the planning, an initial registration can be made in which the recordings of the marks 11 in the video recording are assigned to the corresponding recordings of the marks 11 in the patient model 4, such as in the X-ray data in the present case. The marks 11 must then also be X-ray-sensitive in addition to being visually discernible.

Alternatively, the registration and/or the matching between the video recording and the patient model 4 may also be object-based without marks. The registration is then made by assignment and/or superpositioning of characteristic anatomical structures such as the patient's eyes, nose and/or mouth in the video recording and in the patient model 4.

This assignment may be performed manually by a user or automatically by pattern recognition algorithms. After the initial recording, the position of the marks 11 in the video recording is tracked by a tracking method so that the direction of viewing 13 the patient model is automatically moved as well, depending on the recording direction 9.

The joint tracking of the recording direction in relation to the object 3 can also take place even without marks 11 by using distinct regions of the object 3, such as the chin 14 and/or the jawbone angle 15. These characteristic regions of the object 3 can be recognized by a computer-assisted pattern recognition algorithm in the video recording. As an alternative to representing the patient model 4 via the monitor 8, at least a portion of the patient model may be projected onto the skin surface of the object 3 via a projector 6 which may be integrated into the handpiece 2. This makes it easier for the treating dentist to plan the dental treatment because the X-ray data of the patient model 4 is displayed directly on the skin surface. The planning can then be performed by means of an optical marker 17, such as a laser pointer, directly on the patient's skin surface. The laser pointer 17 projects a laser point 18, which serves as a cursor, onto the skin surface.

When a button 19 on the laser pointer 17 is operated, a certain structure such as a pattern or a flashing code is projected onto the skin surface. Therefore, in operation of the button 19, a certain planning element 20 such as a comment 21, a mark 22, a model of an implant 23, a model of a denture part 24 or a model of an abutment 25 may be selected and inserted into the patient model 4 which is shown. As long as the button 19 remains depressed, the selected planning element 20 can be displaced and positioned in a certain position in relation to the patient model 4. When the button 19 is released, the respective planning element 20 is then released from the laser point 18, and the position of the planning element 20 is thereby defined.

Alternatively, the choice and insertion of the planning element 20 into the patient model 4 can be done on the monitor 8 via a cursor 28 by using input means such as a keyboard 26 and a mouse 27. During the planning, for example, a first finding 29 of a tooth with caries may be provided with a mark 30 by the marking tool 22 and with a comment 31 in text form. The comment 31 can be entered by the user via the keyboard 26 and may contain, for example, information about the finding and about the position
of the respective tooth. A second finding 32 of a tooth affected at the side can be provided with a mark 23 and a comment 34 accordingly. In the last step of the planning, a region 35 where a tooth is missing may be provided with an additional comment 36, and an implant 37 to be inserted, an abutment 38 to be inserted and a denture part 39 to be inserted are then planned. The corresponding models 23, 24 and 25 are then adapted in their dimensions and/orientations to the dental situation.

The advantage of this method is thus that the analysis of findings and the planning of a treatment can take place directly during the video recording. This shortens the treatment time and facilitates the orientation for the treating dentist.

Alternatively or in addition to representation via the monitor 8, the planning elements 20 can also be projected by the projector 16 onto the skin surface 3.

Figure 2:
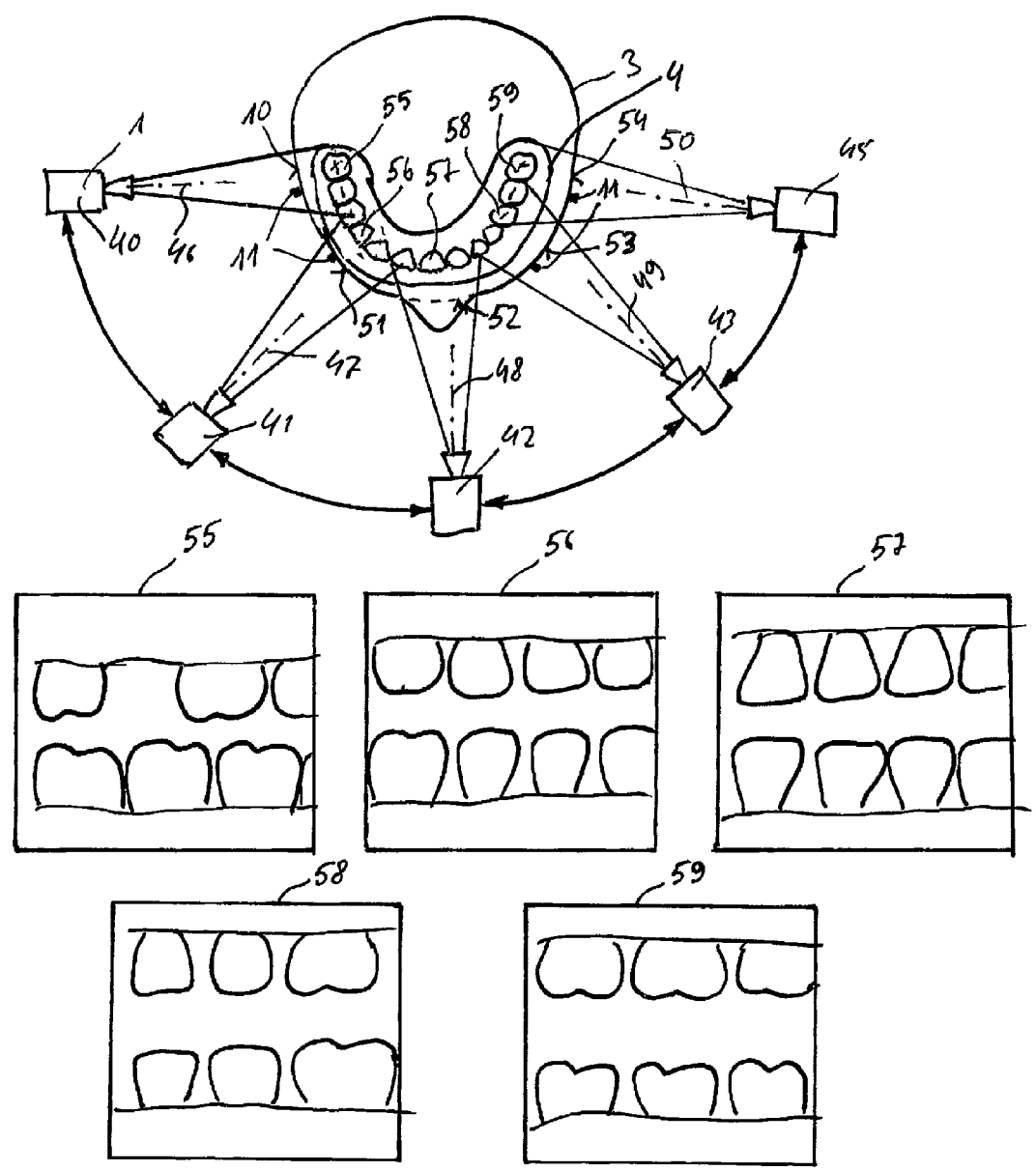
FIG. 2 shows a diagram to illustrate the video recording from various recording directions.

FIG. 2 shows a diagram to illustrate the video recording from various recording directions. The video camera 1 is moved around the object 3 and, in doing so, is positioned in a first position 40, in a second position 41, in a third position 42, in a fourth position 43 and in a fifth position 45. In doing so, the video camera 1 creates the video recording from a first recording direction 46 of the object 3, from a second recording direction 47, from a third recording direction 48, from a fourth recording direction 49 and from a fifth recording direction 50. In doing so, a first section 10, a second section 51, a third section 52, a fourth section 53 and a fifth section 54 of the skin surface of the patient 3 are recorded. The position of the video camera in relation to the patient 3 can be determined on the basis of the marks 11 made on the patient 3. Next, as explained in FIG. 1, the fitting section of the patient model 4 and the X-ray data can be displayed on the monitor 8. In the present case, a first section 55 of the patient model 4 is displayed in the first position 40 of the video camera, a second section 56 is displayed in the second position 41, a third section 57 in the third position 42, a fourth section 58 in the fourth position 53, and a fifth section 59 in the fifth position 45.

REFERENCE NUMERALS

1 Video camera
2 Handpiece
3 Object/head
4 Patient model
5 Computer
6 Cable connection
7 Path of movement
8 Monitor
9 Recording direction
10 First section of the object
11 Mark
12 Second section of the patient model
13 Direction of viewing the patient model
14 Chin
15 Jawbone angle
16 Projector
17 Marker/laser pointer
18 Optical/laser point
19 Button
20 Planning element
21 Comment
22 Mark
23 Implant
24 Denture part
25 Abutment
26 Keyboard
27 Mouse
28 Cursor
30 Mark
31 Comment
32 Second finding
34 Comment
35 Region
36 Comment
37 Implant
38 Abutment
39 Denture part
40 First position
41 Second position
42 Third position
42 Fourth position
45 Fifth position
46 First recording direction
47 Second recording direction
48 Third recording direction
49 Fourth recording direction
50 Fifth recording direction
51 Second section of the object
52 Third section of the object
53 Fourth section of the object
54 Fifth section of the object
56 Second section of the patient model
57 Third section of the patient model
58 Fourth section of the patient model
59 Fifth section of the patient model

The invention claimed is:

1. A dental imaging method, comprising:
   receiving a video recording of an object from a video camera;
   displaying, on a display device or the object, a patient model of the object;
   linking a viewing direction of the patient model, that is displayed on the display device or the object, with a recording direction of the video camera; and
   changing the viewing direction of the patient model in response to a change in the recording direction of the video camera from a first recording direction to a second recording direction such that the viewing direction of the patient model corresponds to the second recording direction of the video camera.

2. The method according to claim 1, wherein the patient model includes three-dimensional optical surface data, three-dimensional X-ray data, virtual planning data and/or MRI scan data of at least one part of the object.

3. The method according to claim 1, further comprising:
   displaying on the display device the video recording superimposed on the patient model.

4. The method according to claim 1, further comprising:
   detecting marks applied to the object or characteristic structures of the object in the video recording using pattern recognition algorithms,
   wherein the viewing direction of the patient model is linked to the recording direction of the video camera, in the linking, based on the marks applied to the object or the characteristic structures of the object.

5. The method according to claim 4, further comprising:
tracking the marks applied to the object or the characteristic structures of the object to determine relative motion between the video camera and the object.

6. The method according to claim 1, further comprising:
causing the display device to display a planning element for a dental restoration superimposed on the patient model, which is also displayed on the display device, during the video recording.

7. The method according to claim 6, wherein the planning element is one of: a virtual mark, a user comment, a drawing of a denture part or implant, or a model of a denture part or implant, and
wherein a position of the planning element is defined in relation to the patient model.

8. The method according to claim 1, further comprising:
causing a projector to display a planning element for a dental restoration on the object.

9. The method according to claim 8, further comprising:
detecting an optical marker, projected onto the object, in the video recording.

10. The method according to claim 9, wherein the optical marker is a laser dot.

11. The method according to claim 1, further comprising:
detecting an optically recognizable marker in the video recording.

12. The method according to claim 11,
wherein the optically recognizable marker is a pen with a colored tip, a finger, or a dental instrument.

13. The method according to claim 9, further comprising:
receiving a signal indicating a selection of the planning element;
receiving a signal indicating a desired position of the planning element; and
determining, when the signal indicating the desired position of the planning element is received, a position of the optical marker in video recording,
wherein a position of the planning element in relation to the patient model is defined by the position of the optical marker in the video recording.

14. The method according to claim 13, wherein the patient model is displayed on the object.

15. The method according to claim 2, further comprising:
causing the three-dimensional optical surface data, the three-dimensional X-ray data, the virtual planning data and/or the MRI scan data of the patient model to be projected onto the object.

16. A dental planning system, comprising:
a camera configured to generate video image data of an object; and
a computer configured to:
receive the video image data of the object from the camera,
cause a patient model of the object to be displayed on a display device or the object,
link a viewing direction of the patient model, that is displayed on the display device or the object, with a recording direction of the camera, and
change the viewing direction of the patient model in response to a change in the recording direction of the camera from a first recording direction to a second recording direction such that the viewing direction of the patient model corresponds to the second recording direction of the camera.

17. The dental planning system according to claim 16, wherein the patient model includes image data of the object.

18. The dental planning system according to claim 17, wherein the image data is one of: three-dimensional optical surface data, three-dimensional x-ray data, or MRI scan data.

19. The dental planning system according to claim 17, wherein the patient model includes a planning element, and
wherein the planning element is one of: a virtual mark, a user comment, a drawing of an dental implant, or a model of a dental implant.

20. The dental planning system according to claim 16,
wherein the computer is further configured to detect marks on the object or characteristic structures of the object from the video image data.

21. The dental planning system according to claim 20, wherein the viewing direction of the patient model is calculated based on the marks on the object or the characteristic structures of the object.

22. The dental planning system according to claim 20, wherein the computer is further configured to determine corresponding regions in the video image data and the patient model based on (i) pattern recognition algorithms and (ii) the marks on the object or the characteristic structures of the object.

23. The dental planning system according to claim 22, wherein the computer is further configured to determine the recording direction of the camera by tracking the marks on the object or the characteristic structures.

24. The dental planning system according to claim 16, wherein the computer is further configured to cause the display device to display a planning element for a dental restoration superimposed on the patient model.

25. The dental planning system according to claim 24, wherein the planning element is one of: a virtual mark, a user comment, a drawing of a denture part or implant, or a model of a denture part or implant, and
wherein a position of the planning element is defined in relation to the patient model.

26. The dental planning system according to claim 16, further comprising:
a projector, and
wherein the computer is further configured to cause the projector to display a planning element for a dental restoration.

27. The dental planning system according to claim 26, further comprising:
an optical marker device configured to project an optical marker onto the object,
wherein the computer is further configured to detect the optical marker in the video image data of the object.

28. The dental planning system according to claim 27, wherein the optical marker device is a laser pointer, and the optical marker is a laser dot.

29. The dental planning system according to claim 27, wherein the optical marker device is further configured to generate a signal indicating a desired position of the planning element and transmit the signal to the computer,
wherein the computer is further configured to determine, when the signal is received, a position of the optical marker in the video image data of the object, and
wherein the position of the planning element in relation to the patient model is defined by the position of the optical marker in the video image data.

* * * * *